United States Patent [19]

Puyana

[11] 4,243,028
[45] Jan. 6, 1981

[54] THERAPEUTIC PRESSURE STRAP

[76] Inventor: Alfonso Puyana, 444 W. 24th St., Yuma, Ariz. 85364

[21] Appl. No.: 46,349

[22] Filed: Jun. 7, 1979

Related U.S. Application Data

[63] Continuation of Ser. No. 912,882, Jun. 5, 1978, abandoned, which is a continuation of Ser. No. 745,646, Nov. 29, 1976, abandoned.

[51] Int. Cl.³ .............................................. A61F 13/00
[52] U.S. Cl. ..................................... 128/165; 128/327
[58] Field of Search ............... 128/165, 327, 155, 156, 128/95, 96

[56] References Cited

U.S. PATENT DOCUMENTS

| | | | |
|---|---|---|---|
| 2,271,927 | 2/1942 | Saighman | 128/327 |
| 3,521,623 | 7/1970 | Nichols et al. | 128/95 X |
| 3,586,001 | 6/1971 | Sanderson | 128/327 |
| 3,954,109 | 5/1976 | Patel | 128/327 |
| 3,970,081 | 7/1976 | Applegate, Jr. | 128/165 X |

FOREIGN PATENT DOCUMENTS

| | | | |
|---|---|---|---|
| 403889 | 10/1924 | Fed. Rep. of Germany | 128/327 |
| 290046 | 11/1931 | Italy | 128/327 |
| 115789 | 5/1918 | United Kingdom | 128/327 |

*Primary Examiner*—John D. Yasko
*Attorney, Agent, or Firm*—Brown & Martin

[57] ABSTRACT

A therapeutic pressure strap primarily for the purpose of treating "tennis elbow" includes a flexible inelastic band having fastening means on both ends thereof for fastening around either the upper or lower extremities of a person, and includes a pressure concentrating portion on the inside of the strap for concentrating pressure on the particular portions of the extremity. The pressure applying portion includes a pair of resilient cylinders enclosed within a pocket. Alternate constructions show the cylinders to be either hollow or solid depending upon the force of the pressure to be applied.

6 Claims, 4 Drawing Figures

THERAPEUTIC PRESSURE STRAP

This is a continuation of application Ser. No. 912,882, filed June 5, 1978, which was a continuation of application Ser. No. 745,646, filed Nov. 29, 1976, both now abandoned.

BACKGROUND OF THE INVENTION

The present invention relates to therapeutic devices and pertains particularly to a therapeutic pressure strap for treating "tennis elbow".

The pathological condition frequently referred to as "tennis elbow" afflicts many people. This is primarily because of the popularity of tennis as a social game, which is played by people who are not in top physical condition. This pathological condition is a painful inflammation of the arm at the elbow. This inflammation is believed to result from the stretching of the tendons which has its point of origin on or at the elbow. It has been discovered that the application of pressure by means of a strap to this area can provide relief from the pain thereof.

Many proposed constructions of straps for this purpose are known. The prior art approach to this problem is exemplified by the following U.S. patents:

U.S. Pat. No. 3,789,842 issued Feb. 5, 1974 to Froimson;

U.S. Pat. No. 3,877,426 issued Apr. 15, 1975 to Nirschl;

U.S. Pat. No. 3,942,525 issued Mar. 9, 1976 to Dragan; and

U.S. Pat. No. 3,970,031 issued July 20, 1976 to Applegate, Jr.

Other straps of somewhat similar construction for other purposes are as follows:

U.S. Pat. No. 3,570,496 issued Mar. 16, 1971 to Sachs;

U.S. Pat. No. 3,586,001 issued June 22, 1971 to Sanderson.

Still other patents of interest are the following:

U.S. Pat. No. 222,754 issued Dec. 16, 1879 to Vaughan et al;

U.S. Pat. No. 3,086,529 issued Apr. 23, 1963 to Munz et al;

U.S. Pat. No. 3,570,495 issued Mar. 16, 1971 to Wright;

U.S. Pat. No. 3,699,945 issued Oct. 24, 1972 to Hanafin;

U.S. Pat. No. 3,930,506 issued Jan. 6, 1976 to Overend.

While these many constructions each provide some form of relief for this problem, there is still considerable room for improvement. Accordingly, it is desirable that an improved and more effective device be provided for relieving the pain of tennis elbow.

SUMMARY AND OBJECTS OF THE INVENTION

It is the primary object of the present invention to overcome the above problems of the prior art.

It is another object of the present invention to provide a therapeutic strap having improved localized pressure applying means for alleviating the pain of tennis elbow.

A further object of the present invention is to provide an improved strap of the therapeutic type or having means for concentrating the pressure for the relief of tennis elbow.

In accordance with the primary aspect of the present invention, the therapeutic strap comprises a flexible non-elastic band having fastening means on opposite ends thereof and means for localizing and concentrating pressure located on the inside of the strap for applying against a particular point.

BRIEF DESCRIPTION OF THE DRAWING

The above and other objects and advantages of the present invention will become apparent from the following description when read in conjunction with the drawings wherein.

DETAILED DESCRIPTION OF A PREFERRED EMBODIMENT

Figure 1:
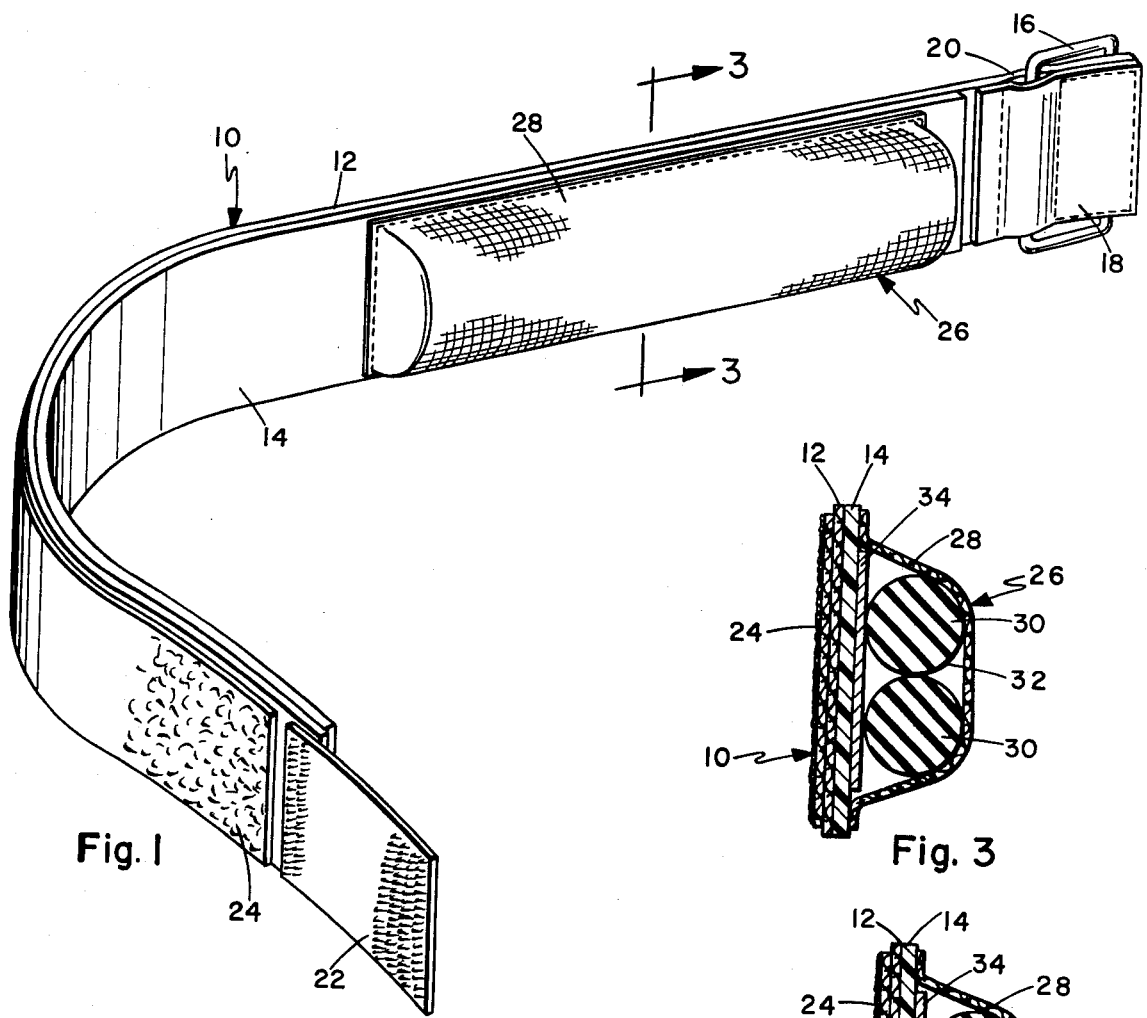
FIG. 1 is a perspective view of a preferred embodiment of the present invention.
Figure 3:
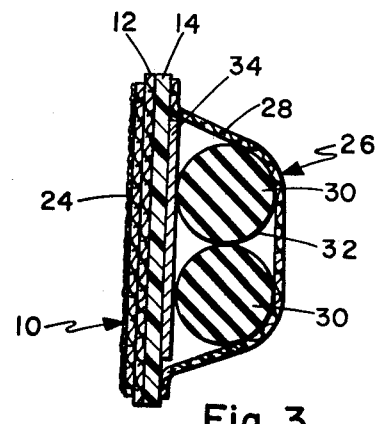
FIG. 3 is a view taken on lines 3—3 of FIG. 1.

Turning now to the drawing, there is illustrated in FIG. 1 a strap in accordance with the present invention designated generally by the numeral 10 and comprising a flexible non-elastic band 12 of sufficient length to encircle the largest expected extremity to be treated. The band may be constructed of any suitable flexible inelastic material such as fabric, vinyl, leather, etc. The band may be lined on the inside with a suitable lining material, such as a thin layer of foam 14 or the like.

The strap includes fastening means on opposite ends thereof for adjustably fastening the strap about an arm or the like. Suitable strap fastening means may be for example, such as a metal loop 16 attached such as by means of a strip of the band material 18 sewn to the band to provide a tube 20 extending transverse thereof through which the metal loop extends. A Velcro type fastener may be utilized on the opposite end of the band, including a strip of hook portion 22 and a strip of fiber loop portion 24. The fiber loop portion 24 may extend substantially along the entire length of the band as illustrated for providing the maximum range of adjustment.

The strap of the present invention includes pressure applying or concentrating means indicated generally by the numeral 26 comprising a pocket 28 formed by a suitable material such as a fabric forming an elongated pocket extending along the band 12 for receiving and confining a pair of adjacently positioned cylindrical resilient members 30. In a preferred embodiment, these cylindrical members are preferably solid so that a much greater amount of pressure may be applied by adjustment of the strap. It should be understood that these members 30 need not necessarily be cylindrical in configuration but are conveniently so selected to provide an outer substantially cylindrical pressure applying surface directed toward and along the inside of the strap. These substantially cylindrical surfaces 32 help concentrate and localize the pressure applied by the strap.

A backing plate 34 may be provided between the cylindrical members 30 and the band 12 of the strap. This backing plate may be constructed of any suitable material, such as metal or plastic and should be of a somewhat flexible nature. This backing plate further helps to localize the pressure only on the side of the arm or limb to which the pad is applied and prevents dissipation of pad pressure through the band portion of the strap.

Figure 4:
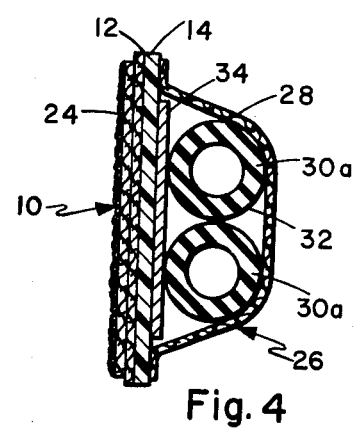
FIG. 4 is a view like FIG. 3 of an alternate embodiment.
Figure 2:
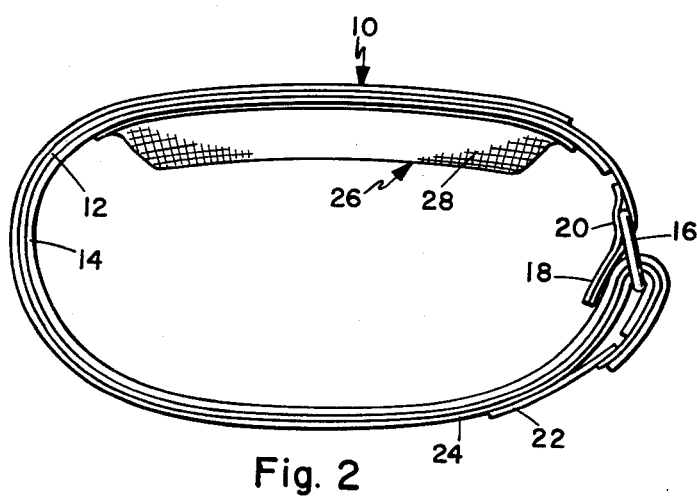
FIG. 2 is a top plan view of the embodiment of FIG. 1 of the looped or closed position.

Turning now to FIG. 4, there is illustrated an alternate embodiment, wherein like numerals are used for the same elements. In this embodiment, the distinction lies in the construction of the cylindrical members 30a being of a tubular configuration. This tubular configuration provides a little greater flexibility in the application of lesser amounts of pressure as needed. This provides a little more flexibility or resilience of the pressure applying portion or pad 26.

While the present invention has been described and illustrated by means of specific embodiments, it is to be understood that numerous changes and modifications may be made herein without departing from the spirit and scope of the invention as defined in the appended claims.

Having described my invention, I now claim:

1. A therapeutic pressure strap adapted for applying concentrated localized pressure to the muscles of a limb for alleviating pathological lesions, said pressure strap comprising:

an elongated flexible inelastic band having an inside and an outside for encircling a human limb with the inside toward the limb, adjustable cooperative fastening means proximate the ends of said band for adjustably fastening said band about the limb and adjusting the pressure applied thereto, an enclosed pocket formed on the inside of said band, and pressure concentrating means protruding from the inside of said band and including at least one elongated resilient self supporting cylindrical pressure member mounted on the inside of said pocket, and having a semi-cylindrical pressure surface extending partially along the longitudinal axis of said band for engaging and concentrating pressure on and across a selected area of the muscles of a limb encircled by said strap.

2. The pressure strap of claim 1, wherein said pressure concentrating means consists solely of a pair of resilient cylinders mounted in said pocket and extending parallel to the longitudinal axis of said band.

3. The pressure strap of claim 2 wherein said cylinders are solid in cross-section.

4. The pressure strap of claim 2 wherein said cylinders are hollow in cross-section.

5. The pressure strap of claim 1 including a backing plate disposed between said cylinder and said band.

6. The pressure strap of claim 2 including a backing plate disposed between said cylinders and said band.

* * * * *